United States Patent [19]

Yamada

[11] 4,024,315

[45] May 17, 1977

[54] ARTIFICIAL HAIR FOR IMPLANTING IN HUMAN TISSUE

[76] Inventor: Shiro Yamada, No. 31-8, Koboyama, Kobo-cho, Chiryu, Aichi, Japan

[22] Filed: Jan. 16, 1976

[21] Appl. No.: 649,599

Related U.S. Application Data

[62] Division of Ser. No. 581,961, May 28, 1975, abandoned.

[52] U.S. Cl. .............................. 428/399; 428/364; 428/401
[51] Int. Cl.² ..................... B32B 27/00; D02G 3/00
[58] Field of Search .......... 428/400, 401, 397, 399, 428/395, 394, 364; 264/145; 156/72, 148

[56] References Cited

UNITED STATES PATENTS

| 3,553,003 | 1/1971 | Carlton et al. | 428/400 |
| 3,684,474 | 8/1972 | Chisholm | 264/145 |
| 3,790,434 | 2/1974 | Sone et al. | 428/400 |

*Primary Examiner*—Lorraine T. Kendell
*Attorney, Agent, or Firm*—Browdy and Neimark

[57] ABSTRACT

A method of implanting artificial hairs in human tissue is disclosed. An artificial hair has a root at one end which is set under the epidermis with a needle means. The needle means has its point shaped for holding an artificial hair at the neck of the root. The root is thrusted into an upper region of the hypodermal layer with the needle means. Withdrawing the needle means leaves the root in position, with its tip end turned back, thus permitting the hair to be firmly implanted.

6 Claims, 14 Drawing Figures

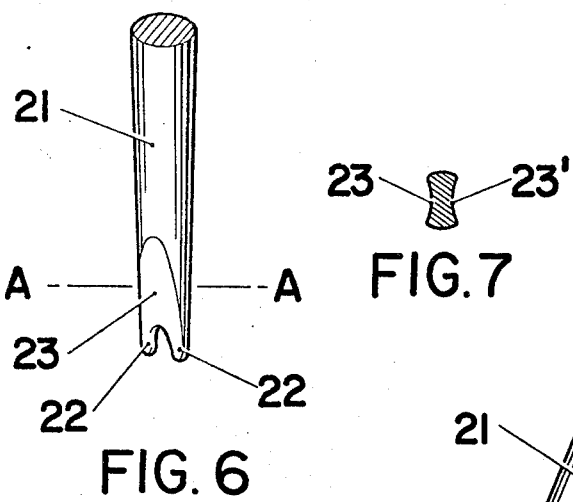
FIG. 6
FIG. 7
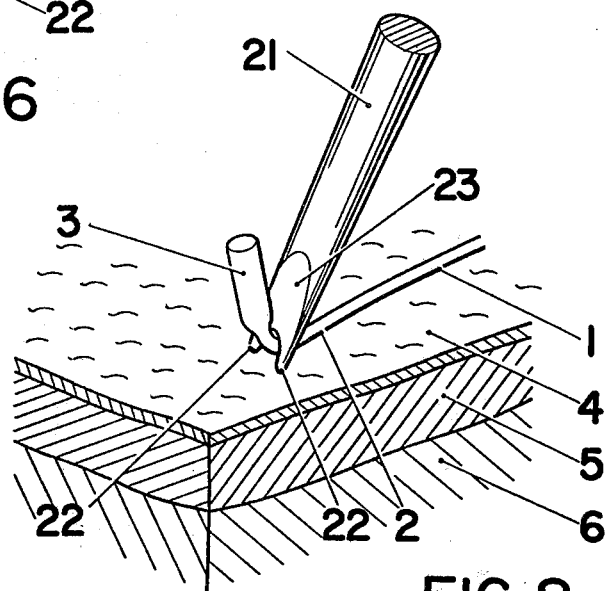
FIG. 8
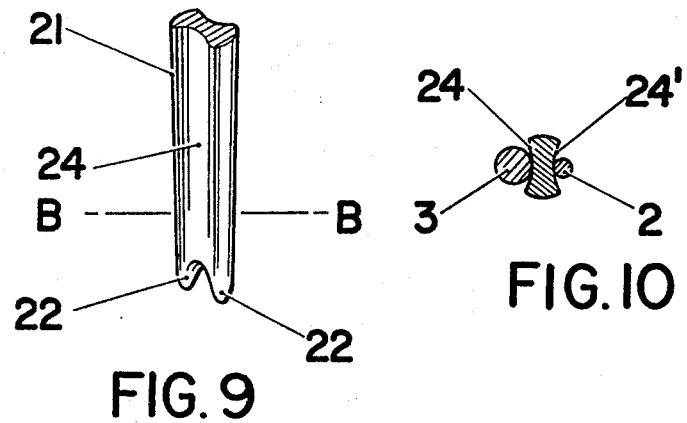
FIG. 9
FIG. 10

ARTIFICIAL HAIR FOR IMPLANTING IN HUMAN TISSUE

This is a division of application Ser. No. 581,961, filed May 28, 1975.

BACKGROUND OF THE INVENTION

1. Field of the Invention

The present invention relates to methods of implanting artificial hairs in human tissue. The invention relates also to devices useful for methods of implanting artificial hairs in human tissue, and to artificial hairs implanted.

2. Description of the Prior Art

Hair transplanting techniques have been known in the field of dermatology. Hair transplantation is a process of removing tufts of hair and their follicles from one place and implanting them in another on the same body. According to this dermatological approach, however, hairs cannot be transplanted without their follicles, and transplanting of other's hair or animal hair will bring about rejection in the recipient tissue.

In place of natural hair transplantation, the use of artificial hair implanted on a cloth has become popular. This approach, however, is far from ideal because of the fact that the hair-implanted cloth, which is bonded to the skin, easily comes off due to spoil by secretions on the skin and due to elasticity disagreement between the cloth and the skin. This type of substitute is useful but for temporary purposes only.

SUMMARY OF THE INVENTION

It is therefore an object of the invention to provide a technique for firmly implanting artificial hairs directly under the epidermis of a human body without causing rejection in the recipient tissue.

It is another object of the invention to provide a device for implanting artificial hairs directly in the dermal or hypodermal tissue.

It is still another object of the invention to provide artificial hair suited to be implanted directly under the epidermis.

With these and other objects in view, the invention provides an artificial hair implanting method in which a needle is used to thrust one end of an artificial hair into the dermal or hypodermal tissue and fix it there. To prevent the implanted hair from falling, the hair has a root at its implanted end which turns back as the needle advances, thus serving as a stopper for the hair. For this purpose, the needle has its point shaped for holding an artificial hair at the root to allow the root to be firmly retained in position when the needle is withdrawn.

Thrusting the root into the skin will cause the outer skin to be broken radially. The area of broken skin, or virtually a tiny spot of cut, is restored perfectly in a few days. In the process of restoration, the tissue about the root and the bottom of the hair implanted is reinforced to hold the hair with a strength greater than a force required to pull out a natural hair from the scalp.

The artificial hair used for the purpose of the invention is of a thermoplastic resin such as nylon and polyacrylonitrile resin. A monofilament of 0.06 to 0.10 mm in diameter is spun out of a material resin by usual melt-spinning and drawing processes. The root is formed of the same resin and connected to the filament by a suitable bonding agent or thermal melting. The root may be formed by heating an end of the filament. The heated part, when cooled, sets up a root. The root is preferably 1.0 to 2.0 mm in length and 0.20 mm in diameter.

The hair-implanting needle used for the purpose of the invention has its point shaped like a fork to hold the neck of the root. The needle may be a pipe permitting the passage of the hair excepting the root. Needles of other shapes may also be used. For example, the point of the needle may be branched like the nose of a pair of pincers.

BRIEF DESCRIPTION OF THE DRAWING

FIG. 1 is a sectional view of the needle through which a hair is extended,

FIG. 2 is a sectional view of the needle holding the root at its point, and FIGS. 3, 4 and 5 are sectional views showing the process of implanting a hair with the needle, FIGS. 6 through 10 illustrate how an artificial hair is implanted with a needle having a fork point; FIG. 6 is a sketch showing the fork part thereof, FIG. 7 is a sectional view through A—A line of FIG. 6, FIG. 8 is a perspective view showing the fork with which a hair is held at the root for implantation, FIG. 9 is a perspective view showing a modified fork part of the needle embodying the invention, and FIG. 10 is a sectional view showing the fork as in FIG. 9, with which an artificial hair is held, FIG. 11 is a perspective view of the pincers holding a hair, and FIG. 12 is a partially enlarged view of the pincers, FIG. 13 is a sectional view of the needle, and FIG. 14 is a sectional view showing a hair which is ready to be implanted with the needle.

DESCRIPTION OF THE PREFERRED EMBODIMENTS

The artificial hair of the invention is of a thermoplastic resin. The resin used for an embodiment is 6—6 nylon to which 2 wt% carbon black is added as a color material. Monofilaments are spun out of this resin by the use of a melt-spinner with a platinum spinning nozzle having 5,000 injection holes each being 0.15 mm in diameter. The monofilaments injected from the spinner are cooled and taken up by a drawing drum. In this process, each monofilament is drawn to a diameter of 0.085 mm. This monofilament is cut to a length, for example, of 120 mm. One end of the cut monofilament is held with pincers, about 5 to 6 mm away of the tip end. This end portion is exposed instantaneously to hot air of 150° C to melt the resin, and thus a root 0.15 mm in diameter and 1.5 mm in length is formed.

Figure 1:
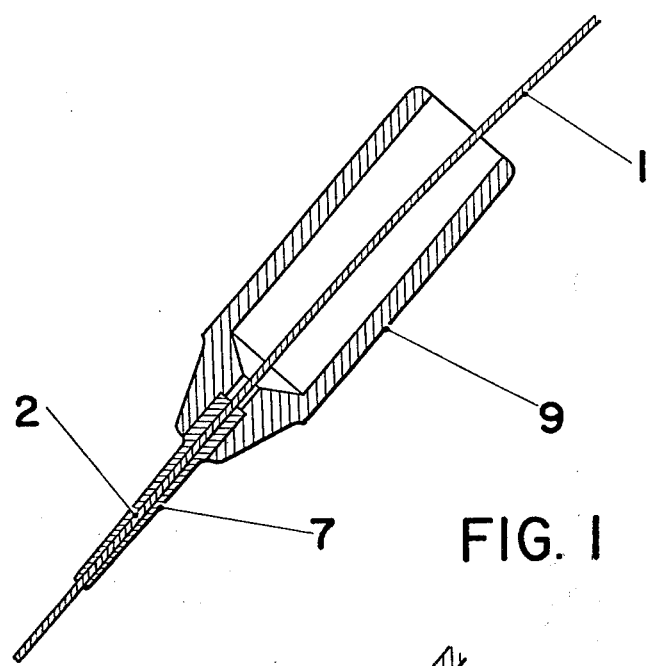
FIGS. 1 through 5 are schematic diagrams illustrating how an artificial hair is implanted with a pipe needle according to the invention.
Figure 2:
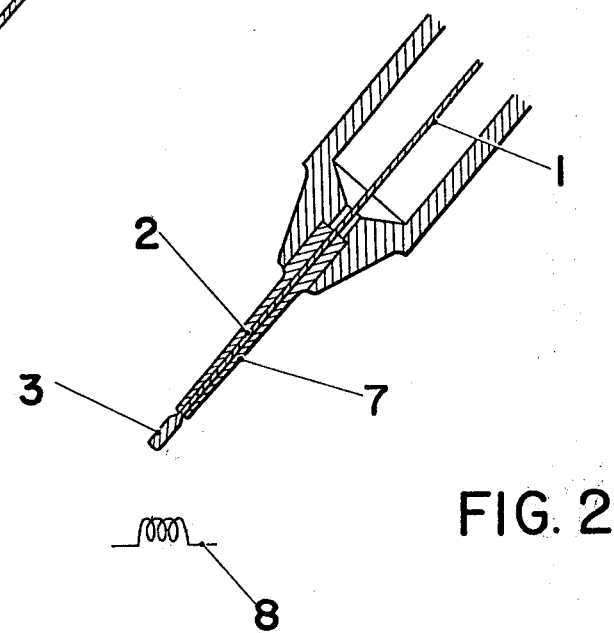

A pipe needle embodying the invention for implanting artificial hair will be described by referring to FIGS. 1 through 5. The nylon monofilament 0.085 mm in diameter obtained by the process described above is used as an artificial hair for the purpose of the invention. This artificial hair 1 is extended through a pipe needle 7 until the tip end comes out to a length of about 6 mm. The protruded part is heated, such as with a heating coil 8, to form a root about 1.5 mm in length and 0.15 mm in diameter as shown in FIG. 2. The root 3 is slightly round at the top and tapered in the neck to fit the point of the needle 7.

Figure 3:
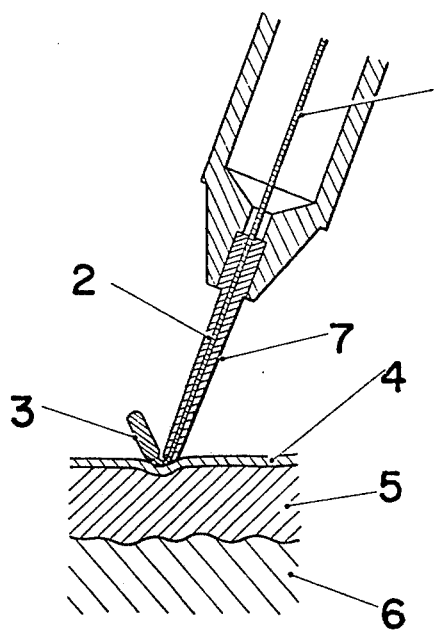
Figure 4:
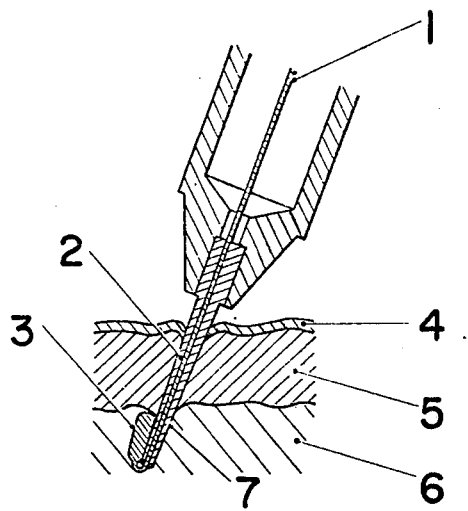
Figure 5:
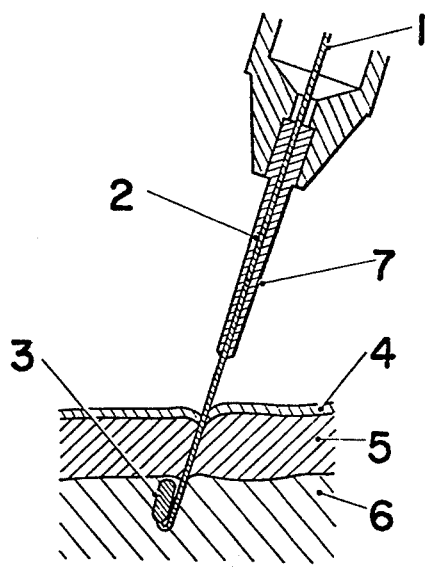

Then, as shown in FIG. 3, the needle is pointed to the scalp 4 where the hair 1 is implanted. The tilt of the needle with respect to the surface of scalp 4 is 40° to 90°. Lightly pressing the needle point against the scalp will cause the root 3 to be turned back outwardly along the needle. Then, as shown in FIG. 4, the needle is thrusted into the scalp 4 until its point reaches a hypodermal tissue layer 6 by way of a dermal layer 5. Then the needle 7 is withdrawn whereby the tip end of the hair 1 is set in position. The root 3 which has been turned back is firmly retained in the dermal and hypodermal layers. The part of the hair 1 above the scalp is cut to a suitable length. Instead of the cut hair 1, a long hair wound on a reel may be used. This arrangement will obviate the need for repetition of tedious procedures for extending an artificial hair through the pipe needle each time it is implanted. In FIG. 4, a similar holder for the needle 7 is shown. The point of the needle 7 is slightly round to minimize epidermal damages caused when it is thrusted into the scalp. A sharp point will tear the skin surface, with the result that restoration is retarded.

Besides forming the root 3, other shapes may be made at the tip end of the hair by heat welding, to meet optimum implanting conditions for individual applications.

Another needle for implanting artificial hair according to the invention will be described by referring to FIGS. 6 through 10. This needle 21 has a fork point 22, with a cross-section shown in FIG. 7 which is viewed through A—A line of FIG. 6. The surfaces 23 and 23' of the fork portion are concave, having a curvature radius approximately equal to the radius of the needle 21.

FIG. 8 illustrates how an artificial hair 1 is implanted in the scalp with the needle 21. The hair 1 is laid on the scalp 4, the neck of the root 3 is held between fork arms 22, the fork point is slightly pressed against the scalp, with the needle titled at an angle of 40° to 90° with the surface of the scalp, and the root is thrusted into the scalp. As a result, the root 3 turns back outwardly along the fork surface 23 as the needle point advances. The trunk 2 of the hair 1 moves along the needle 21 and is pressed into the scalp 4. The needle is further thrust until the root 3 reaches an upper area of the hypodermal tissue 6 by way of the dermal layer 5. Then the needle 21 is withdrawn and the root and base portion of the hair is fixed therein. The hair thus implanted is cut to the desired length above the scalp.

As described above, the root 3 and the trunk 2 move in contact with the concave surfaces 23 and 23'. This makes it possible to reduce the diameter of the tip end of the needle, thus minimizing the area of damages of skin caused when the needle is thrusted. The hurt area will be restored within a few days. During restoration, the hurt dermal and hypodermal tissue is reconstructed around the buried part of the hair to firmly retain the root 3 and base portion of the hair 1. The strength with which the hair is retained overcomes the force required to pull out a natural hair from the scalp.

FIG. 9 illustrates another embodiment of the invention. This needle point is similar to that shown in FIG. 6, excepting concave portions 24 and 24' elongated through the length of the needle 21. The cross-section of the needle 21 is like that of a biconcave lens. The trunk 2 and the root 3 touches the concave surfaces 24 and 24' of the needle as shown in FIG. 10 when the needle advances in the dermal layer. This construction permits the diameter of the needle to be further reduced than in the embodiment shown in FIG. 6, with the result that the area hurt by the needle point is minimized and recovery is speeded up.

Figure 11:
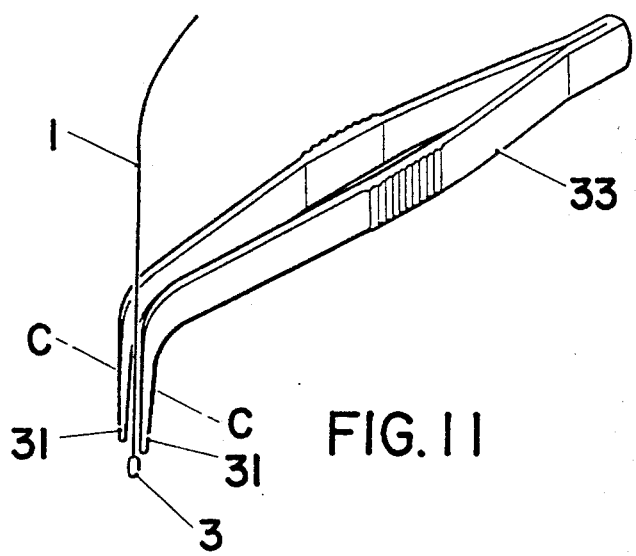
FIGS. 11 and 12 illustrate how an artificial hair is implanted with a pincer means.
Figure 12:
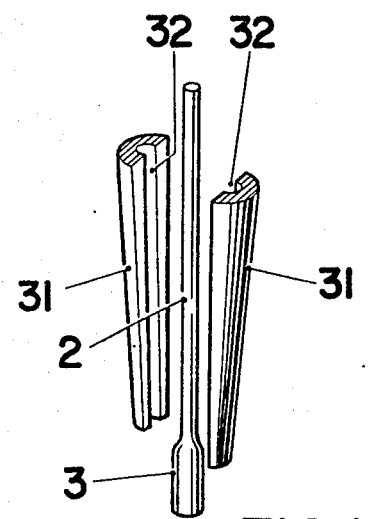

FIG. 11 shows a pincer-like needle embodying the invention, a sectional perspective view of which, taken across C—C, is shown in FIG. 12. A pair of end portions 31 of pincers 33 have longitudinal grooves 32, each being 0.04 to 0.05 mm in radius. The artificial hair is held by the end portions 31 so that its trunk 2 fits in the sheath formed between the grooves 32, and that the root 3 comes out of the tip end of the needle. Then the hair is implanted in the same manner as described hereinbefore.

Figure 13:
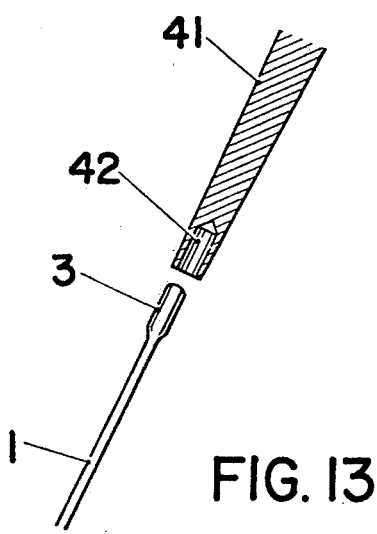
FIGS. 13 and 14 illustrate how an artificial hair is implanted with a needle having a hollow at the point where the root of a hair is held.
Figure 14:
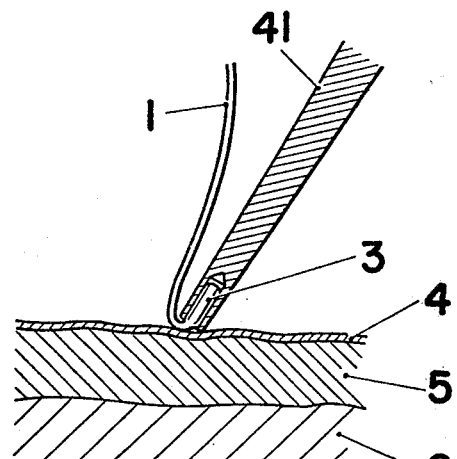

FIGS. 13 and 14 illustrate the construction of another implanting needle of the invention. This needle about 0.25 mm in diameter has a cylindrical hollow 42 at the point. The hollow 42 is about 0.18 mm in diameter and retains the root 3. As shown in FIG. 14, the needle 1 is pointed to the scalp 4 at a tilt of 40° to 90°. Other implanting procedures are the same as those described hereinbefore.

EXPERIMENTS

Implanting nylon hairs with the pipe needle has been experimented:

1. On Animal Skin

Twenty pieces of nylon hair were implanted in each of 6 areas on the back of each of 5 rabbits. Any change in the state of implanted hairs and any possibility of side effect on the skin have been observed for the period of 3 years.

2.

A maximum of 12,000 pieces of nylon hair have been implanted per person, and 70 persons have been registered as recipients of hair implantation in the scalp. No abnormality has ever been observed for 3 years.

The implanted hair can withstand a pull of 55 grams in average, which is well comparable to a force of 35 to 60 grams required to pull out a natural hair from the scalp.

A fall rate of 2 to 3% has been observed. This has been found chiefly due to shallow implantation.

The tissue where the nylon hair was implanted has been pathologically examined and no symptom indicating the development of a malignant tumor has been observed.

While a few preferred embodiments of the invention and specific modifications thereof have been described in detail, it is to be understood that this description is made only for the purpose of illustrating the principles of the invention and not as a limitation on the scope of the invention.

What is claimed is:

1. An artificial hair consisting of a monofilament of 0.06 to 0.10 mm in diameter selected from the group consisting of nylon and polyacrylonitrile resin, said artificial hair having an elongated root formed at one end, said root having a diameter of 0.13 to 0.20 mm and a length of 1.0 to 2.0 mm.

2. An artificial hair in accordance with claim 1 wherein said root has a diameter of about 0.20 mm.

3. An artificial hair in accordance with claim 1 wherein said root has a diameter of about 0.15 mm.

4. An artificial hair in accordance with claim 1 wherein said root is slightly rounded at its free end and is tapered at its end connected with said monofilament.

5. An artificial hair in accordance with claim 1 wherein said root is relatively flat at its free end.

6. An artificial hair in accordance with claim 1 wherein said thermoplastic is nylon 6—6.

* * * * *